United States Patent
Baranger et al.

(10) Patent No.: US 7,262,217 B2
(45) Date of Patent: Aug. 28, 2007

(54) COMPOSITIONS WITH ANISIC ACID AND GLYCERIDES

(75) Inventors: Florence Baranger, Le Vandreuil (FR); Jean Francois Porracchia, Follanvile (FR)

(73) Assignee: Johnson & Johnson Consumer France SAS (FR)

( * ) Notice: Subject to any disclaimer, the term of this patent is extended or adjusted under 35 U.S.C. 154(b) by 176 days.

(21) Appl. No.: 11/010,485

(22) Filed: Dec. 13, 2004

(65) Prior Publication Data

US 2005/0245608 A1    Nov. 3, 2005

(30) Foreign Application Priority Data

Dec. 12, 2003   (EP)   ................ 03293147.9

(51) Int. Cl.
*A61K 31/19* (2006.01)
*A61K 31/22* (2006.01)

(52) U.S. Cl. ............ 514/546; 514/568; 514/419; 514/423; 514/400

(58) Field of Classification Search ........... 514/546, 514/568, 419, 400, 423
See application file for complete search history.

(56) References Cited

U.S. PATENT DOCUMENTS

| | | | | |
|---|---|---|---|---|
| 3,879,542 A | * | 4/1975 | Kaugars | 514/639 |
| 4,645,662 A | | 2/1987 | Nakashima | |
| 5,607,760 A | * | 3/1997 | Roe | 442/375 |
| 5,609,587 A | * | 3/1997 | Roe | 604/360 |
| 6,531,474 B1 | * | 3/2003 | Wannamaker et al. | 514/248 |
| 2004/0167195 A1 | * | 8/2004 | Muller | 514/400 |
| 2005/0147575 A1 | * | 7/2005 | Muller | 424/70.17 |

FOREIGN PATENT DOCUMENTS

| | | |
|---|---|---|
| EP | 884045 A | 12/1998 |
| EP | 1325731 A | 7/2003 |
| GB | 297074 A | 9/1928 |
| JP | 48019940 B | 6/1973 |

* cited by examiner

*Primary Examiner*—Vickie Kim

(57) ABSTRACT

This invention relates to formulations containing a combination of anisic acid, or a salt thereof, or an ester thereof, and a $C_{6-14}$ fatty acid monoglyceride and to the use of such combinations as a preservative system.

8 Claims, No Drawings

COMPOSITIONS WITH ANISIC ACID AND GLYCERIDES

FIELD OF THE INVENTION

This invention relates to formulations containing a combination of anisic acid, or a salt thereof, or an ester thereof, and a $C_{6-14}$ fatty acid monoglyceride and to the use of such combinations as a preservative system.

BACKGROUND OF THE INVENTION

Preservatives are ingredients that have anti-microbial activity that are frequently used in skincare or cosmetic products. Preservatives are aimed at protecting these products from decay or spoilage, so that these products are protected from decomposition and deterioration and remain stable for extended periods of time, in particular during the entire shelf-life of the products.

A disadvantage of using such agents is that they may cause adverse effects such as allergic responses and irritation. Examples of preservatives that are less tolerated especially at increased concentration, are the parabens and phenoxyethanol.

This is especially the case when applying cosmetic formulations containing preservatives to sensitive skin types such as in atopic skin types. This is the reason why so far, cosmetic formulations that can be applied to sensitive skin types (such as, e.g. atopic skin, baby skin, sun alterated skin, allergenic skin) contain less preservatives and therefore are prone to become affected and degraded by microorganisms and moreover to become a source of microbiological contamination.

Preservative agents should by preference be present in as low a concentration as possible. A limiting factor evidently is that the formulations need to be adequately protected. One would therefore be inclined to reduce the amount of preservative in cosmetic formulations, in particular in those formulations that are or can be used on sensitive skin types. By doing so, one could expect that the aforementioned side effects are reduced or even completely absent. However, this would result in the concentration of the preservative being too low to be effective, resulting in an unacceptable risk of the formulation becoming affected by microorganisms.

Therefore it would be desirable to provide formulations for skincare or cosmetic use that are sufficiently protected against microbiological contamination and are not susceptible to microbiological decay and deterioration. It would additionally be desirable to provide such formulations that are devoid of the adverse effects that are typically associated with the use of traditional preservative agents, in particular in the instance of application of cosmetic formulations to sensitive skin types.

Another reason for having low amounts of preservative agents in formulations is that these can interact with certain components present in the formulations, in particular with certain sensitive active ingredients. Certain formulation categories therefore are not easy to preserve. A particular product class is the self-tanning products, in particular those based on dihydroxyacetone (DHA), which is a component that is readily decomposed by physical as well as chemical causes. The presence of certain ingredients in DHA containing formulations promotes decay of this active ingredient and compromises the stability of DHA-based self-tanning formulations.

Hence there is a particular need to have preservative systems that are effective in self-tanning formulations based on DHA.

FR-2 834 459 describes the use of a combination of anisic acid, a salt or an alkyl ester thereof, a polyol and a cationic surfactant as an anti-microbial agent in cosmetic formulations, in particular in hair treatment compositions such as shampoos.

The formulations of the present invention are aimed to meet these needs. The use of a combination of anisic acid and certain fatty acid monoglycerides allows to reduce the amounts of preservative agents in skin care and cosmetic formulations and in particular allows to provide preservative systems in self-tanning formulations based on DHA.

Neither anisic acid nor glyceryl caprilate are currently used as preservatives. Anisic acid is used as fragrance and glyceryl caprilate is used as humectant and emollient.

SUMMARY OF THE INVENTION

The present invention concerns formulations for use on skin comprising a combination of anisic acid, or a salt thereof, or a $C_{1-4}$ alkylester thereof, and a $C_{6-14}$ fatty acid monoglyceride.

In an alternative aspect, this invention concerns the use of a combination of anisic acid, or a salt thereof, or an ester thereof, and a $C_{6-14}$ fatty acid monoglyceride as a preservative system. This invention also concerns the use of a combination of anisic acid, or a salt thereof, or an ester thereof, and a $C_{6-14}$ fatty acid monoglyceride to lower the amount of preservative agents in formulations for topical use.

The present invention concerns formulations for topical use comprising
(a) from 0.01 to 2% of anisic acid, or a salt thereof, or an ester thereof, and a
(b) from 0.1 to 10% $C_{6-14}$ fatty acid monoglyceride.

Preferred are formulations in accordance with the present invention that have a low content of preservative agents.

In a preferred aspect this invention concerns self-tanning formulations containing dihydroxy acetone as self-tanning active ingredient and a combination of anisic acid, or a salt thereof, or an ester thereof, and a $C_{6-14}$ fatty acid monoglyceride.

In another aspect there is provided a formulation as defined herein wherein the preservative is present in an amount that is less than effective.

DETAILED DESCRIPTION OF THE INVENTION

The formulations of this invention contain anisic acid, or o-, m- or p-methoxybenzoic acid, or a salt thereof, or a $C_{1-4}$ alkyl ester thereof. The latter comprise non-toxic salts such as the alkali metal salts in particular the sodium and potassium salts, the alkaline earth metal salts, in particular the magnesium and calcium salts, and the ammonium or derivatized ammonium salts such as the alkylammonium, triethanolamine and the like salts. The $C_{1-4}$ alkyl esters comprise methyl, ethyl, n.propyl, i.propyl, n.butyl, i.butyl and t.butyl esters.

Preferred is p-anisic acid, or a salt thereof, or a $C_{1-4}$ alkyl ester thereof.

The $C_{6-14}$ fatty acid in the monoglycerides are straight or branch chained, saturated or unsaturated, substituted or unsubstituted fatty acids having from about 6 to about 14 carbon atoms. Examples are caproic acid, caprylic acid, capric acid, lauric acid and mylistic acid. Preferred are $C_{6-10}$ fatty acid monoglycerides in particular the $C_8$ fatty acid monoglycerides.

A particularly preferred $C_{6-14}$ fatty acid monoglyceride is glyceryl caprylate.

The anisic acid can be present at concentrations of from 0.01 to 2%, preferably from 0.05 to 5%, more preferably from 0.1 to 1%, e.g. at a concentration of about 0.2%, calculated in relation to the pure acid. In case of salts or of esters these values need to be recalculated accordingly.

The monoglycerides can be present at concentrations of from 0.1 to 10%, preferably from 0.3 to 5%, more preferably from 0.5 to 3%, e.g. at a concentration of about 1%.

In a particular aspect, the present invention concerns formulations for topical use comprising
(a) from 0.01 to 2% of p.-anisic acid, or a salt thereof, or an ester thereof, and
(b) from 0.1 to 10% glyceryl caprylate.

In a further particular aspect, the present invention concerns formulations for topical use comprising
(a) from 0.01 to 2% of p.-anisic acid, or a salt thereof, or an ester thereof, and
(b) from 0.1 to 10% glyceryl caprylate;
(c) less than 1% of preservative agent, in particular less than 0.5% of preservative agent.

Specific embodiments are formulations for topical use comprising
(a) from 0.01 to 2% of p.-anisic acid, or a salt thereof, or an ester thereof, and
(b) from 0.1 to 10% glyceryl caprylate;
(c) less than 0.4% of parabens, or less than 100 ppm iodopropynyl butylcarbamate, or less than 0.5% of phenoxyethanol.

Traditional preservatives comprise phenoxyethanol, alkylparabens and their salts, in particular their alkalimetal salts such as sodium salts (e.g. $C_{1-6}$ alkyl parabens such as methyl, ethyl, propyl, butyl paraben and the like parabens), chlorexidine, and the like, iodopropynyl butylcarbamate, also referred to as butyl-3-iodo-2-propynylcarbamate Still other preservatives are formaldehyde or formaldehyde releasers, e.g. DMDM hydantoin, benzyl alcohol, methylchloroisothiazolinone, methylisothiazolinone, sodium benzoate, chlorhexidine, digluconate, methyldibromo glutaronitrile, 5-bromo-5-nitro-1,3-dioxane, benzoic acid, dehydroacetic acid, diazolidinyl urea, polyaminopropyl biguanide, potassium sorbate, quaternium-15, sorbic acid, triclosan and the like. As used herein the term 'preservative' is meant to also comprise mixtures of preservatives.

The weight by weight ratio of anisic acid and to the total amount of $C_{6-14}$ fatty acid monoglycerides, i.e. anisic acid: $C_{6-14}$ fatty acid monoglycerides may be in the range of from 20:1 to 1:1000, in particular from 15:1 to 1:100, more in particular from 10:1 to 1:30, still more in particular from 1:1 to 1:20, or from 1:1 to 1:10. Preferably said ratio is in the range of from 1:2 to 1:8, for example about 1:5. The weight ratios expressed herein are relative to anisic acid and need be recalculated accordingly when used in salt-form or as an ester.

The term effective preservative activity means that its activity is such that the composition or formulation is protected for a sustained period of time, in particular during the so-called 'shelf life' of the product. The 'shelf-life' of a product is determined according to methods generally known in the art.

The topical formulations of the invention comprise as well dermatological formulations (or topical pharmaceutical formulations), as cosmetical formulations. Said topical formulations may further contain other ingredients or additives used in dermatological or in cosmetical formulations, including other active ingredients.

The formulations according to the present invention are formulated into forms that are useful in cosmetic products. Of particular interest are the formulations that are in emulsion form. The formulations are in particular for application to sensitive skins. Embodiments of particular interest are formulations for use in self-tanning products. These comprise any of the formulations described herein additionally comprising an effective amount of a self-tanning agent, in particular of DHA. Self-tanning formulations in most instances are used on sensitive skin types because users having such skin type want to tan, but do not want or cannot run the risk of skin damage due to exposure to solar radiation.

The self-tanning formulations contain an effective amount of self-tanning active active, in particular of DHA. The self-tanning active ingredient may be present in concentrations which are in the range from 1–10%, preferably 2–8%, e.g. about 5%.

The topical formulations according to the present invention may additionally contain further ingredients or additives such as solvents, surfactants, emulsifiers, consistency factors, conditioners, emollients, skin caring ingredients, moisturizers, thickeners, lubricants, fillers, anti-oxidants, preservatives, active ingredients, in particular dermatologically active ingredients, fragrances and the like.

The formulations may contain surfactants which may be anionic, cationic, non-ionic or amphoteric. Suitable surfactants comprise:
  alkyl sulfates e.g. sodium lauryl sulfate, ammonium lauryl sulfate, sodium cetearyl sulfate,
  alkyl sulfoacetates e.g. sodium lauryl sulfoacetate,
  alkyl ether sulfates e.g. sodium laureth sulfate, sodium trideceth sulfate, sodium oleth sulfate, ammonium laureth sulfate
  alkyl ether sulfosuccinates e.g. disodium laureth sulfosuccinate
  alkyl glycosides e.g. decyl glucoside, lauryl glucoside, alkyl isethionates
  amphoterics, e.g. cocamidopropyl betaine, sodium cocoamphoacetate, sodium lauroamphoacetate, disodium lauroamphodiacetate, disodium cocoamphodiacetate, sodium lauroamphopropionate, disodium lauroamphodipropionate, potassium or ammonium slats of the aforementioned amphoterics, capryl/capramidopropyl betaine, undecylenamidopropyl betaine, lauramidopropyl betaine and
  fatty alcohol polyglycol ethers.

Suitable emulsifiers are e.g. anionics as salts of fatty acids e.g. sodium stearate or sodium palmitate, organic soaps e.g. mono-, di- or triethanolaminoleate, sulfated or sulfonated compounds e.g. sodium lauryl sulfate or sodium cetyl sulfonate, saponines, lamepones; cationics as quaternary ammonium salts; nonionics as fatty alcohols, fatty acid ester with saturated or unsaturated fatty acids, polyoxyethylenesters or polyoxyethylenethers of fatty acids, polymers from ethylene oxide and propylene oxide or propylene glycol, amphotherics as phosphatides, proteines as gelatine, casein alkylamidobetaines, alkyl betaines and amphoglycinates, alkyl phosphates, alkylpolyoxyethylene phoaphates or the corresponding acids, silicone derivatives, e.g. alkyl dimethiconecoplyol.

Suitable consistency factors are e.g. fatty alcohols or their mixtures with fatty acid esters, e.g. acetylated lanolin alcohol, aluminum stearates, carbomer, cetyl alcohol, glyceryl oleate, glyceryl stearate, glyceryl stearate (and) PEG 100 stearate, magnesium stearate, magnesium sulfate, oleic acid, stearic acid, stearyl alcohol, myristyl myristate, isopropyl palmitate, beeswax and synthetic equivalents thereof, carbomers, etc. Suitable conditioners are e.g. alkylamido ammonium lactate, cetrimonium chloride and distearoylethyl hydroxyethylmonium methosulfate and cetearyl alcohol, cetyl dimethicone, cetyl ricinoleate, dimethicone, laureth-23, laureth-4, polydecene, retinyl palmitate, quaternised protein hydrolysates, quaternised cellulose and starch derivatives, quaternised copolymers of acrylic or methacrylic acid or salts, quaternised silicone derivatives.

Suitable emollients are e.g. cetearyl isononanoate, cetearyl octanoate, decyl oleate, isooctyl stearate, coco caprylate/caprate, ethylhexyl hydroxystearate, ethylhexyl isononanoate, isopropyl isostearate, isopropyl myristate, oleyl oleate, hexyl laurate, paraffinum liquidum, PEG-75 lanolin, PEG-7 glyceryl cocoate, petrolatum, ozokerite, cyclomethicone, dimethicone, dimethicone copolyol, dicaprylyl ether, butyrospermum parkii, buxus chinensis, canola, carnauba cera, copernicia cerifera, oenothera biennis, elaeis guineensis, prunus dulcis, squalane, *zea mays*, glycine soja, *helianthus annuus*, lanolin, hydrogenated castor oil, hydrogenated coconut oil, hydrogenated polyisobutene, sucrose cocoate, stearoxy dimethicone, lanolin alcohol, isohexadecane.

Suitable moisturizers are e.g. butylene glycol, cetyl alcohol, dimethicone, dimyristyl tartrate, glucose, glycereth-26, glycerin, glyceryl stearate, hydrolyzed milk protein, lactic acid, lactose and other sugars, laureth-8, lecithin, octoxyglycerin, PEG-12, PEG-135, PEG-150, PEG-20, PEG-8, pentylene glycol, hexylene glycol, phytantriol, polyquaternium-39, PPG-20 methyl glucose ether, propylene glycol, sodium hyaluronate, sodium lactate, sodium PCA, sorbitol, succinoglycan, synthetic beeswax, tri-C14–15 alkyl citrate, starch.

Suitable thickeners are e.g. acrylates/steareth-20 methacrylate copolymer, carbomer, carboxymethyl starch, cera alba, dimethicone/vinyl dimethicone crosspolymer, propylene glycol alginate, hydroxyethylcellulose, hydroxypropyl methylcellulose, silica, silica dimethyl silylate, xanthan gum, hydrogenated butylene/ethylene/styrene copolymer.

Suitable lubricants are e.g. adipic acid, fumaric acid and its salts, glycerine triacetate, sodium or magnesium lauryl sulfate, magnesium stearate, solid polyethylenglycol, polyvinylpyrrolidone, boric acid, monolaurate or -palmitate, myristyl alcohol, cetyl alcohol, cetylstearyl alcohol, talcum, calcium or magnesium salts of higher fatty acids, mono-, di- or triglycerides of higher fatty acids, polytetrafluorethylene.

Examples of active agents for use in the formulations comprise anti-inflammatory agents, anti-irritating compounds, anti-itching agents, moisturising agents, skin caring ingredients, plant extracts, vitamins, actives for anti-stinging, anti-irritants, anti-dandruffs, anti-aging or anti-wrinkling agents, skin lifting agents such as dimethyl amino ethanol (DMAE), and in particular its salt forms. Other suitable actives are e.g. *Medicago officinalis*, allantoin, *Aloe barbadensis, Avena sativa*, beta-carotene, bisabolol, *Borago officinalis*, camphor, cetylpyridinium chloride, *Chamomilla recutita*, copper peptides such as copper tripeptide-1, dichlorophenyl imidazoldioxolan, ethyl panthenol, farnesol, ferulic acid, *Gentiana lutea, Ginkgo biloba, Glycine soya, Hamamelis virginiana*, heliotropine, hydrolyzed wheat protein, lactose, linalool, lysine, magnifera indica, mannitol, menthol, menthyl lactate, olaflur, *Oryza sativa*, panthenol, potassium aspartate, potassium sorbate, *Prunus amygdalus dulcis*, retinoids such as retinal, retinal, retinoic acid, retinol esters such as retinyl palmitate, *Ricinus communis*, salicylic acid, sarcosine, sodium carboxymethyl betaglucan, sodium cocoyl amino acids, sodium hyaluronate, sodium palmitoyl proline, talcum, tocopherol, tocopheryl acetate, tyrosine, urea, valine, zinc oxide, zinc sulfate and the like.

The formulations of the invention can be water-based or can be emulsions, both oil-in-water, and water-in-oil, in aqueous solutions, in PIT (phase inversion temperature) emulsions, in oily solutions, in foaming cosmetic formulations (foams), and in so-called multiple emulsions, e.g. in triple emulsions (such as water/oil/water emulsions). The formulations of the invention can take the form of creams, gels, liquids or lotions. They can be used in shampoos, hair conditioners, hair dyes, hair preparations, aftershave lotions, bath soaps and detergents, fragrance preparations, suncare products, indoor tanning products, body and hand preparations, personal cleansers, shaving preparations, tonics, dressings and other hair grooming aids, moisturizing preparations, skin care preparations and the like.

The topical formulations of the invention are prepared by mixing the ingredients individually or by group-wise mixing. Further ingredients or a composition of further ingredients may be added afterwards. Solvent may be added after mixing, or the components are mixed while being present in a solvent. A premix of anisic acid, or a salt thereof, or an ester thereof, and a $C_{6-14}$ fatty acid monoglyceride may be prepared first, optionally in mixture with a suitable solvent, whereafter the other components are added.

The formulations of the present invention in particular are useful for application on sensitive skin types, in particular persons with an atopic skin type.

In a further aspect, this invention is concerned with synergistic effects between two agents, anisic acid, or a salt thereof, or an ester thereof, on the one hand, a $C_{6-14}$ fatty acid monoglyceride on the other, in terms of anti-microbiological activity, as well as anti-microbiological spectrum. The use of anisic acid, or a salt thereof, or an ester thereof, and a $C_{6-14}$ fatty acid monoglyceride in cosmetic formulations results in both a broad anti-microbial protection and a good skin tolerance. The anti-microbial protection is as well against bacteria as fungi in particular against species such as, for example, *Pseudomonas aeruginosa, Escherichia coli, Staphyococcus aureus, Candida albicans, Aspergillus niger.*

The combinations of anisic acid, or a salt thereof, or an ester thereof, and glyceryl caprilalate can be used as a preservative system in formulations for use on the skin such as in personal care or cosmetic formulations, Said combinations allow to reduce the amount of traditional preservatives in such formulations, or even leave out completely such traditional preservatives, and additionally are useful in formulations for application on sensitive skin types. Said combinations can in particular be used in formulations containing labile ingredients such as active ingredients that are decomposed by traditional preservative ingredients. An example of such an active ingredient is DHA. Hence the combinations of the present invention may find use in formulations, more in particular in emulsions, for use in self-tanning applications.

Another example of active ingredients are sunscreen filters and therefore the formulations of the inventions may take the form of sunscreen formulations.

The formulations of the invention are particularly attractive since the agents therein have a good anti-microbial action on *Staphylococcus aureus* and fungi such as *Aspergillus niger*. The formulations of the invention therefore are most useful in instances where the amount of parabens needs to be reduced because parabens are typically used to protect against fungi. This is in particular the case with atopic skin types which are prone to develop this kind of bacteria and which have a low tolerance towards parabens.

Thus in a further aspect, this invention concerns the use of the formulations as defined herein for combating microorganisms or preventing the growth thereof on human skin, in particular on atopic skin.

Additionally, the combination of the two agents mentioned herein may have pharmaceutical applications and to that purpose may be formulated in appropriate formulations for topical pharmaceutical applications. Hence in still a further aspect the invention provides topical pharmaceutical compositions comprising a composition as defined herein. The composition is present in an amount to effectively preserve the said pharmaceutical compositions.

The invention is further illustrated by the following example.

EXAMPLE

Self-tanning emulsion

| Ingredients (INCI) | % w/w |
|---|---|
| Aqua | 64.5805 |
| Ethylhexyl Salicylate | 10.00 |
| Dihydroxyacetone | 10.00 |
| Ethylhexyl Stearate | 5.00 |
| Sorbitol | 2.10 |
| Cyclohexasiloxane | 1.90 |
| Arachidyl Alcohol | 1.65 |
| Glyceryl Caprylate | 1.00 |
| Hydrogenated Palm Glycerides Citrate | 0.0255 |
| Behenyl Alcohol | 0.90 |
| Arachidyl Glucoside | 0.45 |
| PEG-100 Stearate | 0.75 |
| Glyceryl Stearate | 0.75 |
| Cetyl Alcohol | 0.50 |
| p-Anisic Acid | 0.20 |
| Disodium EDTA | 0.10 |
| Tocopherol | 0.087 |
| Sodium Hydroxide | 0.007 |
| TOTAL | 100.00 |

A first mixture containing the lipophilic components and a second mixture containing the water and water-compatible ingredients was made. Subsequently, the oil phase was added to the aqueous phase under intense stirring as to build an emulsion.

What is claimed is:

1. A preservative formulation for use on skin comprising a combination of 0.01–2% of anisic acid, or a salt thereof, or a $C_{1-4}$ alkylester thereof; and 0.1–10% of a $C_{6-14}$ fatty acid monoglyceride.

2. A formulation according to claim 1, wherein the formulation further comprises a preservative agent present in an amount that is less than effective.

3. A formulation according to claim 1 or 2, wherein the anisic acid is p-anisic acid, or a salt thereof, or a $C_{1-4}$ alkyl ester thereof.

4. A formulation according to claim 1 or 2, wherein the $C_{6-14}$ fatty acid monoglyceride is caproic acid, caprylic acid, capric acid, lauric acid or myristic acid monoglyceride.

5. A formulation according to claim 2, wherein the $C_{6-14}$ fatty acid monoglyceride is glyceryl caprylate.

6. A formulation according to claim 1 or 2, comprising
   (a) from 0.01 to 2% of p.-anisic acid, or a salt thereof, or an ester thereof, and
   (b) from 0.1 to 10% glyceryl caprylate;
   (c) less than 1% of preservative agent, in particular less than 0.5% of preservative agent.

7. A formulation according to claim 1 or 2, comprising
   (a) from 0.01 to 2% of p.-anisic acid, or a salt thereof, or an ester thereof, and
   (b) from 0.1 to 10% glyceryl caprylate;
   (c) less than 0.4% of parabens, or less than 100 ppm iodopropynyl butylcarbamate, or less than 0.5% of phenoxyethanol.

8. A formulation according to any of the claim 1 or 2, wherein the formulation additionally comprises dihydroxyacetone (DHA).

* * * * *